(12) United States Patent
Farrerons Gallemi et al.

(10) Patent No.: US 6,670,365 B1
(45) Date of Patent: Dec. 30, 2003

(54) SUBSTITUTED IMIDAZO 1,2A}AZINES AS SELECTIVE INHIBITORS OF COX-2

(75) Inventors: Carles Farrerons Gallemi, Canyamars (ES); Ignacio-José Miquel Bono, L'Hospitalet de Llobregat (ES); Ana Maria Fernandez Serrat, Barcelona (ES); Carlos Monserrat Vidal, Barcelona (ES); Carmen Lagunas Arnal, L'Hospitalet de Llobregat (ES); Ferran Gimenez Guasch, Barcelona (ES); Andrés Fernandez Garcia, Barcelona (ES)

(73) Assignee: Laboratorios S.A.L.V.A.T., S.A., Esplugues de Llobregat (ES)

( * ) Notice: Subject to any disclaimer, the term of this patent is extended or adjusted under 35 U.S.C. 154(b) by 0 days.

(21) Appl. No.: 09/762,146

(22) PCT Filed: Jul. 23, 1999

(86) PCT No.: PCT/ES99/00235

§ 371 (c)(1),
(2), (4) Date: Apr. 5, 2001

(87) PCT Pub. No.: WO00/08024

PCT Pub. Date: Feb. 17, 2000

(30) Foreign Application Priority Data

Aug. 3, 1998 (ES) .............................. 9801652

(51) Int. Cl.⁷ .................... C07D 487/04; A61K 31/519; A61P 19/02
(52) U.S. Cl. ................ 514/259.1; 514/259.2; 544/281
(58) Field of Search .......... 544/281; 514/258, 514/259.1, 259.2

(56) References Cited

U.S. PATENT DOCUMENTS 2,785,133 A * 3/1957 Craig et al. .............. 252/152
3,455,924 A 7/1969 Lednicer et al. ......... 260/256.4

FOREIGN PATENT DOCUMENTS

WO 92/10190 6/1992
WO 96/03387 2/1996
WO 96/31509 10/1996

OTHER PUBLICATIONS

McMurray et al. Am. J. Med. Sci. 323(4): 181–189,2002.*

* cited by examiner

Primary Examiner—Mukund J. Shah
Assistant Examiner—Venkataraman Balasubramanian
(74) Attorney, Agent, or Firm—Merchant & Gould P.C.

(57) ABSTRACT

The invention refers to new compounds of formula (I), wherein A and B are selected from the group consisting of N and CH, with the condition that when A is N, B is N; $R^1$ is selected from the group consisting of $CH_3$ and $NH_2$; $R^2$ and $R^3$ are selected from the group consisting of H, $CH_3$, Br, Cl, $COCH_3$ and $OCH_3$; and $R^4$, $R^5$ and $R^6$, are selected from the group consisting of H, F, Cl, Br, (C1–C3)-alkyl, trifluoromethyl, (C1–C3)-alkoxy and trifluoromethoxy. Compounds of formula (I) are prepared by reaction of a substituted aminoazine with a substituted 2-bromo-2-(4-$R^1$-sulfonylphenyl)-1-phenylethanone in a polar solvent. These new compounds inhibit COX-2 with high selectivity over COX-1. They are useful for the treatment of inflamation and/or cyclooxygenase-mediated diseases, having the additional advantage of a reduced potencial for ulcerogenic effects.

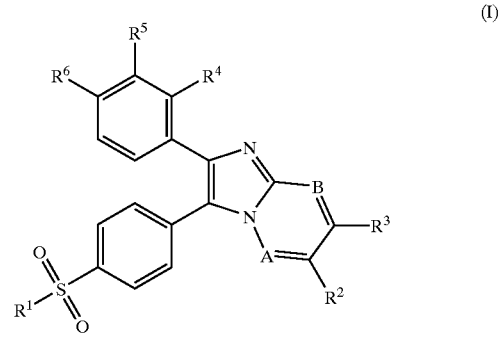

13 Claims, No Drawings

SUBSTITUTED IMIDAZO 1,2A}AZINES AS SELECTIVE INHIBITORS OF COX-2

FIELD OF THE INVENTION

Classically the main mechanism of action of non-steroidal antiinflammatory drugs has been the inhibition of cyclooxygenase. This enzyme transforms the arachidonic acid in prostaglandin $H_2$, that is subsequently transformed into other prostaglandins, prostacyclins or thromboxanes. Recently it has been proved the existence of two cyclooxygenase isoforms, namely COX-1 and COX-2. Although they are equivalent in a 60% of their structure, they have important functional differences.

COX-1 is a constitutive enzyme located in most of the human tissues and it is nowadays considered responsible for the maintenance of several physiological functions. It synthetizes prostanoids in response to the stimulus produced by the circulating hormones that control the physiological cellular processes ($TxA_2$ in platelets, $PGI_2$ in endothelium, $PGE_2$ in kidney and intestinal mucosa, etc). These hormones are necessary for the maintenance of vascular homeostasis and gastric and renal functions.

Very recently, it has been sequenced, characterized and cloned the gene for a second inducible cyclooxygenase form (COX-2). COX-2 is an inducible enzyme, usually undetectable in most of the tissues, but its expression is significantly increased during inflammatory processes. It has been demonstrated that the induction of COX-2 is located in fibroblasts, macrophages, intestinal and bronquial epithellium cells, due to the exposure to proinflammatory agents like endotoxins, cytokines and growth factors. COX-2 expression has been detected in different animal models of acute or chronic inflammation.

The discovery of inducible isoenzyme COX-2, distinct from constitutive enzyme COX-1, has renewed the interest in the development of new non-steroidal antiinflammatory drugs for inflammation therapy, as it is assumed that beneficial action of these drugs will be due to their activity over COX-2, while associated side effects will be due to their activity over COX-1. It is desirable to have new pharmaceutical antiinflammatory drugs with selective inhibition of COX-2 in preference to COX-1. These drugs, with similar antiinflammatory, antipyretic and analgesic properties to conventional non-steroidal antiinflammatory drugs, may have anticancer effects, but with a remarkable decrease of non-desired side effects. In particular, such a compound would have a reduced potential for gastrointestinal toxicity, a reduced potential of renal side effects and a highly reduced effect on bleeding times.

Patent application WO 96/31509 describes imidazo[1,2a] pyridines with 4-sulfonylphenyl radicals at the 2 position of the fused heterocyclic system as selective COX-2 inhibitors, in accordance with the general formula:

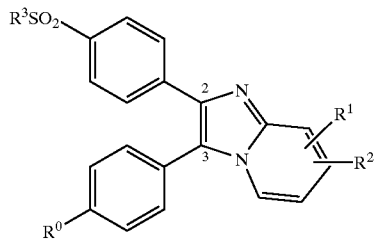

Patent applications WO 92/10190 and WO 96/03387 disclose structurally closed compounds for the treatment of inflammation.

However, the imidazo[1,2a]azines whith 4-sulfonylphenyl radicals at the 3 position (instead of the 2 position) of the fused heterocyclic system which are subject-matter of the present invention have never been chemically described before. They are found to show remarkable and unexpected selective COX-2 inhibition.

SUMMARY OF THE INVENTION

The present invention provides new substituted imidazo [1,2a]azines of formula (I), or a pharmaceutically acceptable acid addition salt and solvates thereof, wherein A and B are independently selected from N and CH, with the condition that when A is N, then B is N too; $R^1$ is selected from the group consisting of $CH_3$ and $NH_2$, preferably $CH_3$; $R^2$ and $R^3$ are selected from the group consisting of H, $CH_3$, Cl, Br, $COCH_3$ and $OCH_3$, preferably H; $R^4$, $R^5$ and $R^6$ are each independently selected from the group consisting of H, F, Cl, Br, (C1–C3)-alkyl, trifluoromethyl, (C1–C3)-alkoxy and trifluoromethoxy. Preferably, $R^4$, $R^5$ and $R^6$ are selected from the group consisting of H, methyl, isopropyl, F, Cl, methoxyl and ethoxyl.

Compounds of formula (I) wherein A is CH and B is N are preferred.

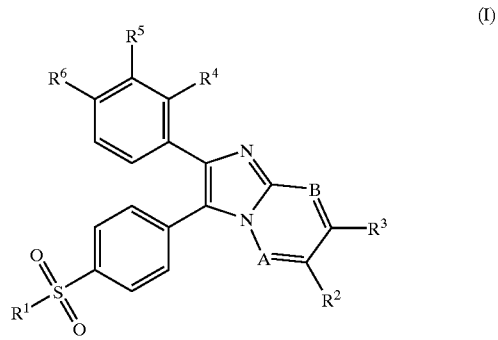

(I)

When A is CH and B is N, the imidazo[1,2a]azines of formula (I) are named imidazo[1,2a]pyrimidines, and the particular examples are listed here by a letter (Ia, Ib, . . . ). When A is N and B is N, the imidazo[1,2a]azines of formula (I) are named imidazo[1,2a]triazines, and the particular examples are listed here by two letters (Iaa, Ibb, . . . ). When A is CH and B is CH, the imidazo[1,2a]azines of formula (I) are named imidazo[1,2a]pyridines, and the particular examples are listed here by three letters (Iaaa, Ibbb, . . . ). To establish the nomenclature of those fused ring systems, it has been used the numeration hereinbelow explained, that is equivalent to that used in WO 96/31509 for compounds with a similar structure.

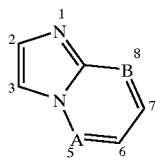

The compounds of formula (I) hereinbelow named are especially preferred, and their nuclear magnetic resonance chemical shifts spectra are described. The ¹H-NMR chemical shifts (δ) are given in parts per million (ppm) with respect to tetramethylsilane (TMS), and NMR have been carried out on a 300 MHz spectrometer, using a suitable deuterated solvent. The following abbreviations are used: s, singlet; d, doublet; t, triplet; q, quadruplet; dd, doublet of doublets; td, triplet of doublets; m, multiplet.

In the present invention the synthesis of some of the following compounds are also described:

(Ia) 2-phenyl-3-(4-methylsulfonylphenyl)imidazo [1,2a] pyrimidine. ¹H RMN (CDCl₃ 300 MHz): δ 3.17 (s, 3H), 6.92 (dd, 1H), 7.32–7.34 (m, 3H), 7.65–7.71 (m, 4H), 8.10 (d, 2H), 8.36 (dd, 1H), 8.62 (dd, 1H).

(Ib) 2-(4-methylphenyl)-3-(4-methylsulfonylphenyl)imidazo[1,2a]pyrimidine. ¹H RMN (CDCl₃ 300 MHz): δ 2.35 (s, 3H), 3.17 (s, 3H), 6.91 (m, 1H), 7.14 (d, 2H), 7.56 (d, 2H), 7.69 (d, 2H), 8.10 (d, 2H), 8.35 (d, 1H), 8.60 (d, 1H).

(Ic) 2-(4-fluorophenyl)-3-(4-methylsulfonylphenyl)imidazo[1,2a]pyrimidine. ¹H RMN (CDCl₃ 300 MHz): δ 3.18 (s, 3H), 6.93 (dd, 1H), 7.00–7.06 (m, 2H), 7.63–7.70 (m, 4H), 8.10 (d, 2H), 8.34 (dd, 1H), 8.63 (dd, 1H).

(Id) 2-(4-chlorophenyl)-3-(4-methylsulfonylphenyl)imidazo[1,2a]pyrimidine. ¹H RMN (DMSO 300 MHz): δ 3.31 (s, 3H), 7.09 (dd, 1H), 7.43 (d, 2H), 7.58 (d, 2H), 7.81 (d, 2H), 8.11 (d, 2H), 8.61–8.66 (m, 2H).

(Ie) 2-(4-bromophenyl)-3-(4-methylsulfonylphenyl)imidazo[1,2a]pyrimidine. ¹H RMN (CDCl₃ 300 MHz): δ 3.18 (s, 3H), 6.97 (dd, 1H), 7.46 (d, 2H), 7.54 (d, 2H), 7.69 (d, 2H), 8.12 (d, 2H), 8.33 (d, 1H), 8.63 (d, 1H).

(If) 2-(4-methoxyphenyl)-3-(4-methylsulfonylphenyl)imidazo[1,2a]pyrimidine. ¹H RMN (CDCl₃ 300 MHz): δ 3.17 (s, 3H), 3.82 (s, 3H), 6.88 (m, 3H), 7.60 (d, 2H), 7.70 (d, 2H), 8.10 (d, 2H), 8.35 (d, 1H), 8.58 (d, 1H).

(Ig) 2-(4-ethoxyphenyl)-3-(4-methylsulfonylphenyl)imidazo[1,2a]pyrimidine. ¹H RMN (CDCl₃ 300 MHz): δ 1.42 (t, 3H), 3.17 (s, 3H), 3.95–4.14 (m, 2H), 6.83–7.00 (m, 3H), 7.60 (d, 2H), 7.69 (d, 2H), 8.10 (d, 2H), 8.33 (dd, 1H), 8.59 (dd, 1H).

(Ih) 2-(3,4-dimethylphenyl)-3-(4-methylsulfonylphenyl)imidazo[1,2a]pyrimidine. ¹H RMN (CDCl₃ 300 MHz): δ 2.24 (s, 3H), 2.26 (s, 3H), 3.17 (s, 3H), 6.91 (m, 1H), 7.03 (d, 1H), 7.21 (d, 1H), 7.64 (s, 1H), 7.70 (d, 2H), 8.10 (d, 2H), 8.35 (d, 1H), 8.61 (s, 1H).

(Ii) 2-(3-methyl-4-methoxyphenyl)-3-(4-methylsulfonylphenyl)imidazo[1,2a]pyrimidine. ¹H RMN (CDCl₃ 300 MHz): δ 2.18 (s, 3H), 3.16 (s, 3H), 3.83 (s, 3H), 6.72 (d, 1H), 6.89 (dd, 1H), 7.31 (dd, 1H), 7,60 (s, 1H), 7.70 (d, 2H), 8.09 (d, 2H), 8.35 (dd, 1H), 8.58 (dd, 1H)

(Ij) 2-(3-fluoro-4-methoxyphenyl)-3-(4-methylsulfonylphenyl)imidazo [1,2a]pyrimidine. ¹H RMN (CDCl₃ 300 MHz): δ 3.19 (s, 3H), 3.90 (s, 3H), 6.88–6.93 (m, 2H), 7.37–7.46 (m, 2H), 7.71 (d, 2H), 8.13 (d, 2H), 8.32 (dd, 2H), 8.61 (dd, 1H).

(Ik) 2-(3-chloro-4-methoxyphenyl)-3-(4-methylsulfonylphenyl)imidazo[1,2a]pyrimidine. ¹H RMN (DMSO 300 MHz): δ 3.31 (s, 3H), 3.85 (s, 3H), 7.06 (dd, 1H), 7.13 (d, 1H), 7.41 (dd, 1H), 7.68 (d, 1H), 7.83 (d, 2H), 8.12 (d, 2H), 8.57–8.62 (m, 2H).

(Il) 2-(3,4-dimethoxyphenyl)-3-(4-methylsulfonylphenyl)imidazo[1,2a]pyrimidine. ¹H RMN (CDCl₃ 300 MHz): δ 3.17 (s, 3H), 3.85 (s, 3H), 3.88 (s, 3H), 6.75 (d, 1H), 6.94–7.02 (m, 2H), 7.51 (d, 1H), 7.76 (d, 2H), 8.13 (d, 2H), 8.34 (dd, 1H), 8.62 (dd, 1H).

(Im) 7-methyl-2-(4-methylphenyl)-3-(4-methylsulfonylphenyl)imidazo [1,2a]pyrimidine. ¹H RMN (DMSO 300 MHz): δ 2.56 (s, 3H), 3.30 (s, 3H), 3.75 (s, 3H), 6.91–6.95 (m, 3H), 7.50 (d, 2H), 7.77 (d, 2H), 8.08 (d, 2H), 8.46 (d, 1H).

(In) 7-methyl-2-(3,4-dimethylphenyl)-3-(4-methylsulfonylphenyl)imidazo[1,2a]pyrimidine. ¹H RMN (CDCl₃ 300 MHz): δ 2.23 (s, 3H), 2.25 (s, 3H), 2.65 (s, 3H), 3.15 (s, 3H), 6.76 (d, 1H), 7.01 (d, 1H), 7.21 (dd, 1H), 7.62 (s, 1H), 7.67 (d, 2H), 8.06 (d, 2H), 8.20 (d, 1H).

(Io) 2-(4-methylphenyl)-3-(4-aminosulfonylphenyl)imidazo[1,2a]pyrimidine. ¹H RMN (DMSO 300 MHz): δ 2.30 (s, 3H), 7.05 (dd, 1H), 7.16 (d, 2H), 7.47–7.49 (m, 4H), 7.72 (d, 2H), 7.99 (d, 2H), 8.57–8.58 (m, 2H).

(Ip) 2-(3-fluoro-4-methoxyphenyl)-3-(4-aminosulfonylphenyl)imidazo[1,2a]pyrimidine. ¹H RMN (DMSO 300 MHz): δ 3.84 (s, 3H), 7.04 (dd, 1H), 7.14 (t, 1H), 7.33 (d, 1H), 7.38 (dd, 1H), 7.50 (s, 2H), 7.74 (d, 2H), 8.01 (d, 2H), 8.54 (dd, 1H), 8.60 (dd, 1H).

(Iq) 2-(2-methylphenyl)-3-(4-aminosulfonylphenyl)imidazo[1,2a]pyrimidine. ¹H RMN (DMSO 300 MHz): δ 2.12 (s, 3H), 7.11–7.27 (m, 5H), 7.39 (s, 2H), 7.55 (d, 2H), 7,86 (d, 2H), 8,20 (d, 1H), 8,64 (d, 1H).

(Ir) 2-(4-fluorophenyl)-3-(4-aminosulfonylphenyl)imidazo[1,2a]pyrimidine. ¹H RMN (DMSO 300 MHz): δ 6.02 (s, 2H), 6.89 (d, 1H), 7.02–7.09 (m, 4H), 7.80 (d, 2H), 8.10 (d, 2H), 8.56–8.60 (m, 2H).

(Is) 2-(2-chlorophenyl)-3-(4-aminosulfonylphenyl)imidazo[1,2a]pyrimidine. ¹H RMN (DMSO 300 MHz): δ 7.09 (dd, 1H), 7.28 (s, 2H), 7.57–7.84 (m, 8H), 8.30 (dd, 1H), 8.67 (dd, 1H).

(It) 2-(3-fluorophenyl)-3-(4-aminosulfonylphenyl)imidazo[1,2a]pyrimidine. ¹H RMN (DMSO 300 MHz): δ 7.08 (s, 1H), 7.16 (s, 1H), 7.39 (m, 3H), 7.51 (s, 2H), 7.76 (d, 2H), 8.02 (d, 2H), 8.57 (d, 1H), 8.64 (s, 1H).

(Iu) 2-(3-chlorophenyl)-3-(4-aminosulfonylphenyl)imidazo[1,2a]pyrimidine. ¹H RMN (DMSO 300 MHz): δ 7.07 (dd, 1H), 7.35–7.44 (m, 3H), 7.51 (s, 2H), 7.69 (s, 1H), 7.75 (d, 2H), 8.01 (d, 2H), 8.57 (dd, 1H), 8.64 (dd, 1H).

(Iaa) 2-phenyl-3-(4-methylsulfonylphenyl)imidazo[1,2a][1,2,4]triazine. ¹H RMN (CDCl₃ 300 MHz): δ 3.15 (s, 3H), 7.37–7.42 (m, 3H), 7.70–7.76 (m, 2H), 7.86 (d, 2H), 8.05 (d, 2H), 8.39 (d, 1H), 8.54 (d, 1H).

(Ibb) 2-(4-fluorophenyl)-3-(4-methylsulfonylphenyl)imidazo[1,2a][1,2,4]triazine. ¹H RMN (CDCl₃ 300 MHz): δ 3.15 (s, 3H), 7.09 (m, 2H), 7.72 (m, 2H), 7.85 (m, 2H), 8.07 (m, 2H), 8.39 (d, 1H), 8.55 (d, 1H).

(Icc) 2-(3-fluoro-4-methoxyphenyl)-3-(4-methylsulfonylphenyl)imidazo[1,2a][1,2,4]triazine. ¹H RMN (CDCl₃ 300 MHz): δ 3.16 (s, 3H), 3.93 (s, 3H), 6.95 (t, 1H), 7.42 (m, 1H), 7.55 (dd, 1H), 7.86 (d, 2H), 8.08 (d, 2H), 8.38 (d, 1H), 8.53 (d, 1H).

(Idd) 2-phenyl-3-(4-aminosulfonylphenyl)imidazo[1,2a][1,2,4]triazine. ¹H RMN (DMSO 300 MHz): δ 7.39–7.41 (m, 3H), 7.51 (s, 2H), 7.64–7.67 (m, 2H), 7.77 (d, 2H), 7.96 (d, 2H), 8.65 (m, 2H).

(Iee) 2-(2-fluorophenyl)-3-(4-aminosulfonylphenyl)imidazo[1,2a][1,2,4]triazine. ¹H RMN (DMSO 300 MHz): δ

7.18–7.25 (m, 1H), 7.32–7.39 (m, 3H), 7.49–7.51 (m, 1H), 7.63–7.64 (m, 2H), 7.70–7.75 (m, 1H), 7.86–7.88 (m, 1H), 8.06 (s, 1H), 8.70–8.73 (m, 2H).

(Iff) 2-(2-chlorophenyl)-3-(4-aminosulfonylphenyl)imidazo[1,2a][1,2,4]triazine. $^1$H RMN (DMSO 300 MHz): δ 7.35 (s, 2H), 7.44–7.60 (m, 4H), 7.65 (d, 2H), 7.84 (d, 2H), 8.72 (d, 1H), 8.77 (d, 1H).

(Igg) 2-(3-methylphenyl)-3-(4-aminosulfonylphenyl)imidazo[1,2a][1,2,4]triazine. $^1$H RMN (DMSO 300 MHz): δ 2.31 (s, 3H), 7.21 (t, 1H), 7.27 (d, 1H), 7.35 (d, 1H), 7.44 (s, 2H), 7.60 (s, 1H), 7.77 (d, 2H), 7.97 (d, 2H), 8.64 (s, 2H).

(Ihh) 2-(3-fluorophenyl)-3-(4-aminosulfonylphenyl)imidazo[1,2a][1,2,4]triazine. $^1$H RMN (DMSO 300 MHz): δ 7.18–7.25 (m, 1H), 7.43–7.46 (m, 5H), 7.78 (d, 2H), 7.99 (d, 2H), 8.66 (d, 2H).

(Iaaa) 2-phenyl-3-(4-methylsulfonylphenyl)imidazo[1,2a]pyridine. $^1$H RMN (CDCl$_3$ 300 MHz): δ 3.17 (s, 3H), 6.88 (td, 1H), 7.27–7.36 (m, 4H), 7.58–7.62 (m, 2H), 7.70 (d, 2H), 7.81 (d, 1H), 8.05–8.11 (m, 3H).

(Ibbb) 2-(4-fluorophenyl)-3-(4-methylsulfonylphenyl)imidazo[1,2a]pyridine. $^1$H RMN (CDCl$_3$ 300 MHz): δ 3.21 (s, 3H), 6.88 (m, 1H), 7.03 (t, 2H), 7.33 (t, 1H), 7.58 (m, 2H), 7.69 (d, 2H), 7.78 (d, 1H), 8.05–8.12 (m, 3H).

(Iccc) 2-(4-methoxyphenyl)-3-(4-methylsulfonylphenyl)imidazo[1,2a]pyridine. $^1$H RMN (CDCl$_3$ 300 MHz): δ 3.17 (s, 3H), 3.82 (s, 3H), 6.78–6.90 (m, 3H), 7.27 (m, 3H), 7.52 (d, 2H), 7.65–7.74 (m, 3H), 8.02–8.12 (m, 3H).

(Iddd) 2-(4-ethoxyphenyl)-3-(4-methylsulfonylphenyl)imidazo[1,2a]pyridine. $^1$H RMN (CDCl$_3$ 300 MHz): δ 1.41 (t, 3H), 3.16 (s, 3H), 4.04 (q, 2H), 6.78–6.88 (m, 3H), 7.26 (ddd, 1H), 7.50 (d, 2H), 7.54–7.64 (m, 3H), 8.02–8.10 (m, 3H).

(Ieee) 2-(4-isopropoxyphenyl)-3-(4-methylsulfonylphenyl)imidazo [1,2a]pyridine. $^1$H RMN (CDCl$_3$ 300 MHz): δ 1.34 (d, 6H), 3.17 (s, 3H), 4.56 (m, 1H), 6.82–6.88 (m, 3H), 7.27–7.33 (m, 1H), 7.52 (d, 2H), 7.70 (d, 2H), 7.78 (d, 1H), 8.04–8.11 (m, 3H).

(Ifff) 2-(3-methyl-4-methoxyphenyl)-3-(4-methylsulfonylphenyl)imidazo[1,2a]pyridine. $^1$H RMN (CDCl$_3$ 300 MHz): δ 2.20 (s, 3H), 3.16 (s, 3H), 3.83 (s, 3H), 6.72 (d, 1H), 6.83 (td, 1H), 7.21–7.30 (m, 2H), 7.54 (m, 1H), 7.68–7.76 (m, 3H), 8.04–8.10 (m, 3H).

(Iggg) 2->(3-fluoro-4-methoxyphenyl)-3-(4-methylsulfonylphenyl)imidazo[1,2a]pyridine. $^1$H RMN (CDCl$_3$ 300 MHz): δ 3.18 (s, 3H), 3.89 (s, 3H), 6.83 (td, 1H), 6.89 (t, 1H), 7.24–7.32 (m, 3H), 7.68–7.74 (m, 3H), 8.03 (d, 1H), 8.10 (d, 2H).

(Ihhh) 2-(3-chloro-4-methoxyphenyl)-3-(4-methylsulfonylphenyl)imidazo[1,2a]pyridine. $^1$H RMN (CDCl$_3$ 300 MHz): δ 3.17 (s, 3H), 3.91 (s, 3H), 6.82–6.87 (m, 2H), 7.26–7.37 (m, 2H), 7.68–7.74 (m, 4H), 8.04 (d, 1H), 8.10 (d, 2H).

(Iiii) 2-(3.4-dimethoxyphenyl)-3-(4-methylsulfonylphenyl)imidazo[1,2a]pyridine. $^1$H RMN (CDCl$_3$ 300 MHz): δ 3.16 (s, 3H), 3,83 (s, 3H), 3.88 (s, 3H), 6.77 (d, 1H), 6.83 (td, 1H), 6.98 (dd, 1H), 7.29–7.34 (m, 2H), 7.72 (d, 2H), 7.78 (d, 1H), 8.05 (d, 1H), 8.10 (d, 2H).

(Ijjj) 7-methyl-2-(4-methoxyphenyl)-3-(4-methylsulfonylphenyl)imidazo[1,2a]pyridine. $^1$H RMN (CDCl$_3$ 300 MHz): δ 2.43 (s, 3H), 3.16 (s, 3H), 3.81 (s, 3H), 6.65 (dd, 1H), 6.85 (d, 2H), 7.50 (m, 3H), 7.66 (d, 2H), 7.94 (d, 1H), 8.05 (d, 2H).

(Ikkk) 6-methyl-2-(4-ethoxyphenyl)-3-(4-methylsulfonylphenyl)imidazo[1,2a]pyridine. $^1$H RMN (CDCl$_3$ 300 MHz): δ 1,41 (t, 3H), 2.32 (s, 3H), 3.18 (s, 3H), 4.03 (q, 2H), 6.84 (d, 2H), 7.15 (dd, 1H), 7.50 (d, 2H), 7.66–7.69 (m, 3H), 7.81 (s, 1H), 8.08 (d, 2H).

(Illl) 6-chloro-2-(4-ethoxyphenyl)-3-(4-methylsulfonylphenyl)imidazo[1,2a]pyridine. $^1$H RMN (CDCl$_3$ 300 MHz): δ 1.41 (t, 3H), 3.18 (s, 3H), 4.04 (q, 2H), 6.84 (d, 2H), 7.03 (dd, 1H), 7.49 (d, 2H), 7.68 (m, 3H ), 8.04 (d, 1H), 8.11 (d, 2H).

(Immm) 6-bromo-2-(4-ethoxyphenyl)-3-(4-methylsulfonylphenyl)imidazo[1,2a]pyridine. $^1$H RMN (CDCl$_3$ 300 MHz): δ 1.41 (t, 3H), 3.18 (s, 3H), 4.04 (q, 2H), 6.84 (d, 2H), 7.34 (dd, 1H), 7.49 (d, 2H), 7.63–7.69 (m, 3H), 8.11 (m, 3H).

(Innn) 2-(2-methylphenyl)-3-(4-aminosulfonylphenyl)imidazo[1,2a]pyridine. $^1$H RMN (DMSO 300 MHz): δ 2.08 (s, 3H), 6.98 (t, 1H), 7.15–7.23 (m, 4H), 7.37 (m, 3H), 7.52 (d, 2H), 7.68 (d, 1H), 7.84 (d, 2H), 8.42 (d, 1H).

(Iooo) 2-(2-fluorophenyl)-3-(4-aminosulfonylphenyl)imidazo[1,2a]pyridine. $^1$H RMN (DMSO 300 MHz): δ 7.01 (t, 1H), 7.14 (t, 1H), 7.27 (m, 1H), 7.38–7.42 (m, 4H), 7.54–7.74 (m, 4H), 7.89 (m, 2H), 8.28 (d, 1H).

(Ippp) 2-(3-methylphenyl)-3-(4-aminosulfonylphenyl)imidazo[1,2a]pyridine. $^1$H RMN (DMSO 300 MHz): δ 2.27 (s, 3H), 6.92 (t, 1H), 7.07–7.25 (m, 3H), 7.34 (m, 1H), 7.48 (s, 2H), 7.53 (s, 1H), 7.66–7.71 (m, 3H), 7.99 (d, 2H), 8.12 (dd, 1H).

(Iqqq) 2-(3-fluorophenyl)-3-(4-aminosulfonylphenyl)imidazo[1,2a]pyridine. $^1$H RMN (DMSO 300 MHz): δ 6.93 (td, 1H), 7.09–7.15 (m, 1H), 7.32–7.39 (m, 4H), 7.57 (s, 2H), 7.68–7.74 (m, 3H), 8.01 (d, 2H), 8.11 (d, 1H).

(Irrr) 2-phenyl-3-(4-aminosulfonylphenyl)imidazo[1,2alpyridine. $^1$H RMN (DMSO 300 MHz): δ 6.92 (td, 1H), 7.28–7.37 (m, 4H), 7.48 (s, 2H), 7.57 (dd, 2H), 7.66–7.71 (m, 3H), 8.00 (d, 2H), 8.11 (d, 1H).

(Isss) 2-(4-fluorophenyl)-3-(4-aminosulfonylphenyl)imidazo[1,2a]pyridine. $^1$H RMN (DMSO 300 MHz): δ 6.92 (t, 1H), 7.18 (t, 2H), 7.35 (t, 1H), 7.55–7.59 (m, 4H), 7.67–7.72 (m, 3H), 7.99 (d, 2H), 8.12 (d, 1H).

(Ittt) 2-(4-methoxyphenyl)-3-(4-aminosulfonylphenyl)imidazo[1,2a]pyridine. $^1$H RMN (DMSO 300 MHz): δ 3.75 (s, 3H), 6.90 (d, 3H), 7.33 (t, 1H), 7.48–7.51 (m, 4H), 7.64–7.71 (m, 3H), 8.00 (d, 2H), 8.10 (d, 1H).

(Iuuu) 2-(3-methyl-4-methoxyphenyl)-3-(4-aminosulfonylphenyl)imidazo[1,2a]pyridine. $^1$H RMN (DMSO MHz): δ 2.11 (s, 3H), 3.77 (s, 3H), 6.83–6.89 (m, 2H), 7.22–7.31 (m, 2H), 7.48 (m, 3H), 7.62–7.70 (m, 3H), 7.89 (d, 2H), 8.09 (d, 1H).

(Ivvv) 2-(3-fluoro-4-methoxyphenyl)-3-(4-aminosulfonylphenyl)imidazo[1,2a]pyridine. $^1$H RMN (DMSO 300 MHz): δ 3.83 (s, 3H), 6.91 (td, 1H), 7.11 (t, 1H), 7.27–7.39 (m, 3H), 7.49 (s, 2H), 7.66 (d, 1H), 7.71 (d, 2H), 8.01 (d, 2H), 8.08 (d, 1H).

(Iwww) 2-(3-chloro-4-methoxyphenyl)-3-(4-aminosulfonylphenyl)imidazo[1,2a]pyridine. $^1$H RMN (DMSO 300 MHz): δ 3.84 (s, 3H), 6.92 (td, 1H), 7.09 (m, 1H), 7.31–7.41 (m, 2H), 7.49 (s, 2H), 7.64–7.74 (m, 4H), 8.01 (d, 2H), 8.09 (d, 1H).

(Ixxx) 2-(3,4-difluorophenyl)-3-(4-aminosulfonylphenyl)imidazo[1,2a]pyridine. $^1$H RMN (DMSO 300 MHz): δ 6.94 (t, 1H), 7.33–7.41 (m, 2H), 7.50 (s, 2H), 7.53–7.58 (m, 1H), 7.67–7.74 (m, 3H), 8.02 (d, 2H), 8.10 (d, 1H).

Compounds 2-(4-fluorophenyl)-3-(4-methylsulfonylphenyl)imidazo[1,2a]pyrimidine (Ic), 2-(4-methoxyphenyl)-3-(4-methylsulfonylphenyl)imidazo[1,2a]pyrimidine (If), and 2-(4-ethoxyphenyl)-3-(4-ethylsulfonylphenyl)imidazo[1,2a]pyrimidine (Ig), that have an specially selective COX-2 inhibitory activity, as shown in Table 1, are even more preferred.

A suitable method for the preparation of substituted imidazo[1,2a]azines of formula (I) is object of this invention. This method includes the condensation of an aminoazine of formula (III) with a 2-bromo-2-(4-$R^1$-sulfonylphenyl)-1-phenylethanone of formula (II), in a polar solvent.

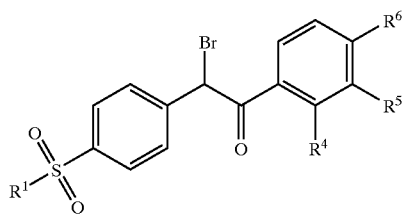
(II)

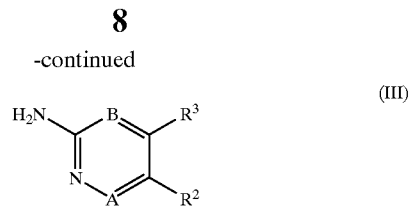
(III)

Intermediates (II) and (III) are obtained from known compounds.

When $R^1$ is $CH_3$, the new substituted imidazo[(1,2a] azines of formula (I, $R^1$=$CH_3$) may be prepared according to the synthetic procedure shown in Scheme 1, that is being applied to the next three paragraphs.

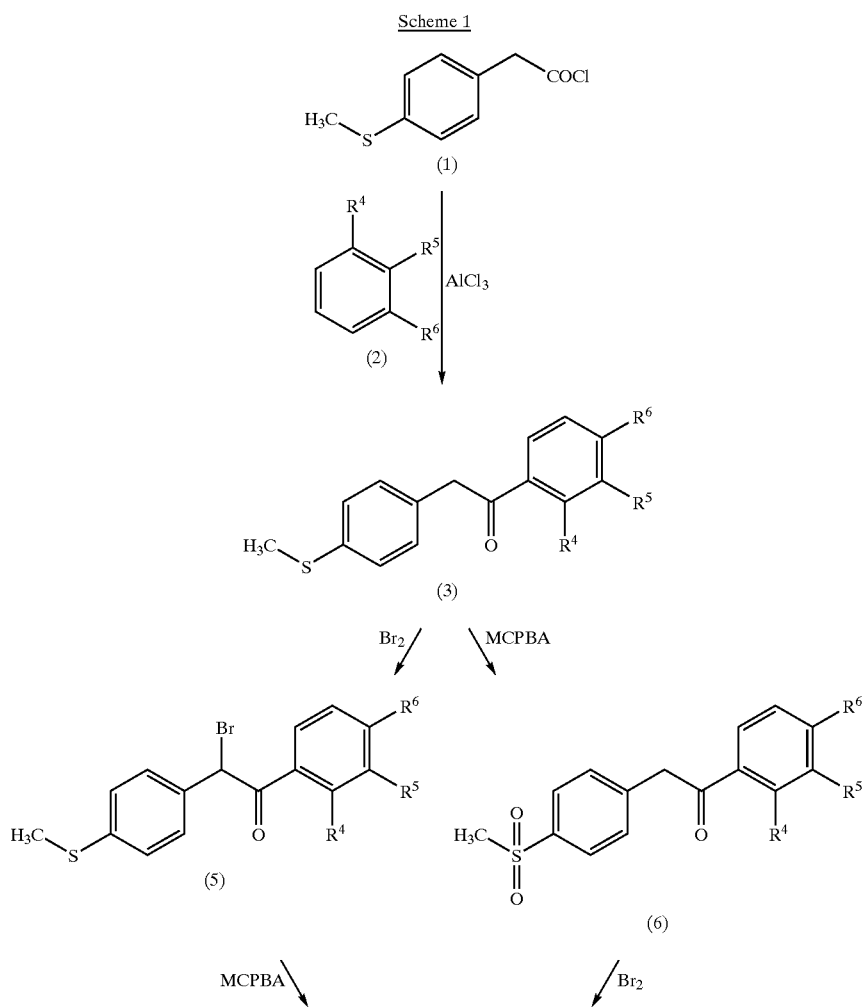

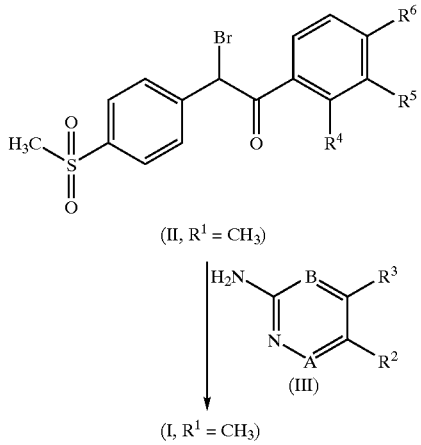

(II, R¹ = CH₃)

(III)

(I, R¹ = CH₃)

| Product | COX-2(IC₅₀;µM) | COX-1(IC₅₀;µM) |
| --- | --- | --- |
| (Ia) | 5.5 | >50 |
| (Ib) | 10 | >50 |
| (Ic) | 2.9 | >50 |
| (Id) | >10 | >50 |
| (If) | 1.4 | 25 |
| (Ig) | 1.0 | 50 |
| (Ih) | 2.8 | >50 |
| (Ii) | 2.2 | 30 |
| (Ik) | 3.9 | 61 |
| (In) | 4.2 | 2 |
| (Io) | 4.5 | >50 |
| (Is) | 10 | 100 |
| (It) | 10 | 50 |
| (Iaa) | 3.1 | 76 |
| (Ibb) | 2.2 | 50 |
| (Idd) | 3.8 | >50 |
| (Igg) | 2.8 | 10 |
| (Ihh) | 10 | 100 |
| (Iccc) | 3.3 | 40 |
| (Iddd) | 3.5 | 80 |
| (Ifff) | 1.0 | 45 |
| (Ihhh) | 6.8 | 82 |
| (Innn) | >5 | >100 |
| (Ippp) | 3.1 | 50 |
| (Iqqq) | >10 | >100 |
| (Iuuu) | 1.7 | 25 |
| Indomethacin | 0.4 | 0.21 |

When $R^1$ is $CH_3$, $R^6$=(C1–C3)-alkoxy and trifluoromethoxy, and $R^4$ and $R^5$ are independently selected from the group consisting of H, F, Cl, Br, (C1–C3)-alkyl, trifluoromethyl, (C1–C3)alkoxy and trifluoromethoxy.

Also, when $R^1$ is $CH_3$, $R^6$=H, F, Cl, Br, (C1–C3)alkyl, trifluoromethyl, (C1–C3)-alkoxy and trifluoromethoxy, $R^4$=$R^5$=H.

Also when $R^1$ is $CH_3$, $R^4$=$R^6$=(C1–C3)-alkyl and $R^5$=H or $R^5$=$R^6$=(C1–C3)-alkyl and $R^4$=H.

The first step is a Friedel-Crafts acylation of the s substituted benzene compound (2) with an acyl halide (1), using dichloromethane, 1,2-dichloroethane or the substituted benzene compound as the solvent, to yield the ketone (3). The thioether of the ketone (3) is then consecutively oxidized to methylsulfone with an oxidizing agent (e.g. m-chloroperoxibenzoic acid (MCPBA), hydrogen peroxyde ($H_2O_2$), or sodium perborate ($NaBO_3$)), and α-brominated, to give substituted 2-bromo-2-(4-methylsulfonylphenyl)-1-phenylethanones (II, $R^1$=$CH_3$) with good yields. In the last step, the bromoketones (II, $R^1$=$CH_3$) were treated with an equimolar or excess amount of aminoazine (III), in a heated (e.g. refluxed) polar solvent (e.g. acetonitrile, ethanol or terbutilic alcohol), optionally in the presence of a base (e.g. potassium carbonate). Compounds (I, $R^1$=$CH_3$) can be isolated as free base, or can be treated with pharmaceutically acceptable acids to give the resulting addition salts.

When $R^1$ is $NH_2$ the new substituted imidazo[1,2a]azines of formula (I, $R^1$=$NH_2$) can be prepared according to the synthetic procedure shown in Scheme 2. The substituted ketones (6) are treated first with chlorosulfonic acid to give the resulting sulfonyl chloride, and with ammonia later to yield the sulfonamides (7). Bromination of the α-carbonylic position yields the substituted 2-bromo-2-(4-aminosulfonylphenyl)-1-phenylethanones (II, $R^1$=$NH_2$).

These compounds are treated with an equimolar amount or excess amount of aminoazine (III), in a heated (e.g. refluxed) polar solvent (e.g. acetonitrile, ethanol or tert-butyl alcohol), optionally in the presence of a base (e.g. potassium carbonate). Compounds (I, $R^1$=$CH_3$) can be isolated as free base, or can be treated with pharmaceutically acceptable acids to give the resulting addition salts.

When (6) is a ketone, where $R^4$=F, Cl, Br, (C1–C3)-alkyl, trifluoromethyl, (C1–C3)-alkoxy and trifluoromethoxy, and $R^5$ and $R^6$ are independently selected from the group consisting of H, F, Cl, Br, (C1–C3)-alkyl; or $R^4$=$R^6$=H, and $R^5$=F, Cl, Br, (C1–C3)-alkyl, trifluoromethyl, (C1–C3)-alkoxy and trifluoromethoxy, the ketones (6) can be prepared according to the method described in Scheme 3. Aldehydes (7) afford the substituted alcohols (9) by addition of the appropriate organomagnesium reagent (8), prepared by treatment of benzyl chloride or bromide with magnesium in tetrahydrofurane or diethyl ether as a solvent.

Subsequent oxidation of the substituted alcohol (9) to the ketone (6) is performed by treatment with an

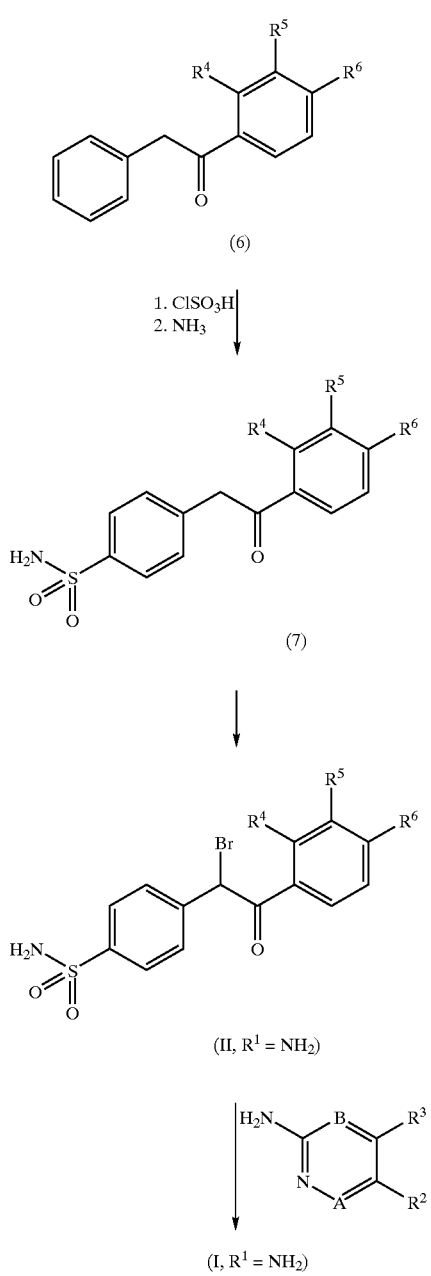

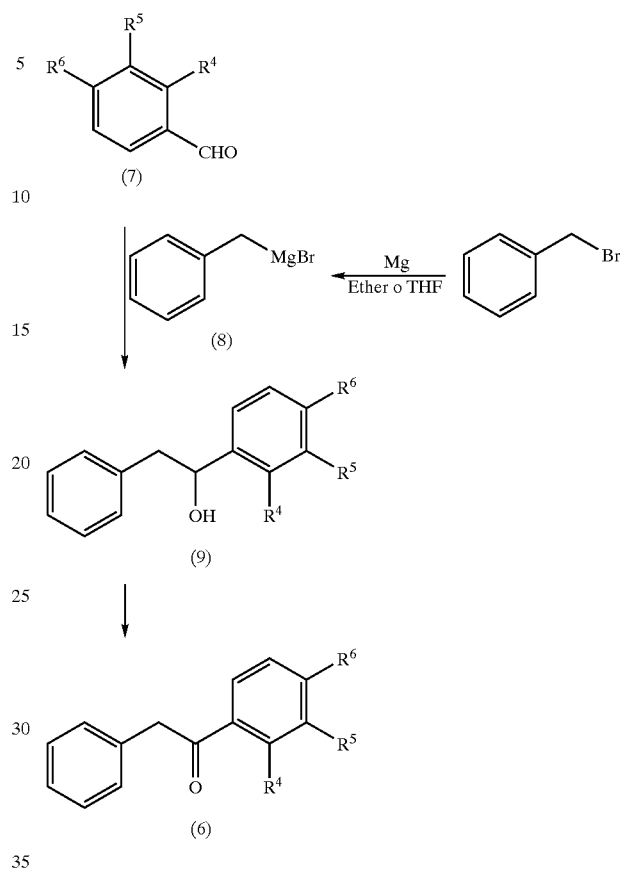

oxidising agent (such as pyridinium chlorochromate or aluminium tert-butoxide).

The substituted imidazo[1,2a]azines of formula (I) inhibit cyclooxygenase-1 and cyclooxygenase-2 (COX-1 and COX-2) in vitro, as shown in Table 1. Compounds (I) selectively inhibit COX-2 in preference to COX-1.

Due to their high selectivity, the compounds herein described are useful as an alternative to conventional non-steroidal antiinflamatory drugs, especially when these drugs may be contra-indicated because of their ulcerogenic side effects.

Compounds of formula (I) can prevent neuronal injury by inhibiting the generation of neuronal free radicals, and they can be useful for the treatment of epileptic seizures.

Compounds of formula (I) previously defined are useful for the treatment of pain, fever and inflammation in a variety of conditions including rheumatic fever, symptoms associated with influenza or other viral infections, common cold, neck pain, dysmenorrhea, headache, toothache, sprains and strains, myositis, neuralgia, synovitis, arthritis, including rheumatoid arthritis, osteoarthritis, gout and ankylosing spondylitis, tendinitis, skin related conditions such as psoriasis, eczema, dermatitis and burns, injuries arising surgical and dental procedures. These compounds may also inhibit cellular and neoplastic transformations and metastatic tumor growth, and hence can be used in the treatment of cancer, such as colon cancer. Compounds of formula (I) can be used in the treatment and/or prevention of cyclooxygenase mediated diseases such as diabetic retinopathy and tumour angiogenesis.

Compounds of formula (I) can also inhibit. prostanoid-induced smooth muscle contraction by preventing the synthesis of contractile prostanoids, and can also be useful for the treatment of dysmenorrhea and premature labour. They are also useful for the treatment of cognitive disorders such as dementia, senile dementia, Alzeihmer's disease, Pick's disease, Parkinson's disease, Creutzfeldt-Jackob disease, and for the treatment of osteoporosis.

Compounds of formula (I) inhibit inflammatory processes and therefore can be useful in the treatment of asthma, allergic rhinitis, respiratory distress syndrome, gastrointestinal conditions such as Crohn's disease, gastritis, inflammatory bowel disease and ulcerative colitis; and inflammation in other diseases such as migraine, periarteritis nodosa, thyroiditis, Hodgkin's disease, sclerodoma, myasthenia gravis, multiple sclerosis, sarcoidosis, nephrotic syndrome, Bechet's syndrome, polymyositis, gingivitis and conjuctivitis.

Compounds of formula (I) can be useful for the treatment of ophthalmic diseases such as retinitis, retinopathies, uveitis, and of acute injury to the eye tissue.

Unless explicitly stated otherwise, it is to be understood that reference to treatment includes both treatment of established symptoms and prophylactic treatment.

The present invention also encompasses the pharmaceutical compositions comprising a therapeutically effective amount of any compound of formula (I), previously defined, in association with suitable amounts of pharmaceutically acceptable carriers. Among them, pharmaceutical compositions for the treatment of inflammation, for the treatment of cyclooxygenase-mediated diseases or for the selective inhibition of cyclooxygenase 2 (COX-2), are specially preferred.

The pharmaceutical compositions of the present invention can be prepared by any form, known in the art, for oral, injectable, rectal or topical administration.

Due to its high COX-2 selectivity, illustrated by data shown in Table 1, the compounds herein described are useful as an alternative to conventional non-steroidal antiinflamatory drugs, especially when these drugs may be contraindicated because of their ulcerogenic side effects. Hence, another embodiment of the present invention is the use of any of the compounds of formula (I), previously defined, for the manufacture of a therapeutic agent for the treatment of inflammation, for the treatment of cyclooxygenase-mediated diseases, for the selective inhibition of cyclooxygenase 2 (COX-2), and for the treatment of cancer, particulary the colon cancer.

EXAMPLES

The following examples illustrate the invention.

Example 1

Preparation of 1-(4-Fluorophenyl)-2-(4-methylthiophenyl) ethanone (Intermediate 3, $R^4=R^5=H$, $R^6=F$)

A mixture of fluorobenzene (181 mL) and aluminum chloride (18.5 g, 139 mmol) was treated with a solution of 4-methylthiophenyl acetic chloride (21.9 g, 120 mmol) in 37 mL of fluorobenzene. When the addition was completed, the mixture was stirred at 50° C. for 3 h. The reaction mixture was then poured into ice water and stirred for 1 h. It was extracted with chloroform and washed with 5% aqueous sodium bicarbonate solution and with brine. The organic layer was separated and dried over anhydrous sodium sulfate. The drying agent was filtered and the filtrate concentrated in vacuum to give 15.6 g (55%) of the desired compound as a yellow solid.

Example 2

Preparation of 1-(4-Fluorophenyl)-2-(4-methylsulfonylphenyl)ethanone (Intermediate 4, $R^4=R^5=H$, $R^1=F$).

A solution of 15.5 g (60 mmol) of 1-(4-fluorophenyl)-2-(4-methylthiophenyl)ethanone in 2 L of chloroform was prepared. 3-Chloroperoxybenzoic acid, 36.5 g (148 mmol), was then portionwise added to the solution. The reaction mixture was stirred for 3 h and treated with 5% aqueous sodium bicarbonate solution. The organic layer was separated and washed with with 5% aqueous sodium bicarbonate solution and with brine. It was dried over anhydrous sodium sulfate. The drying agent was filtered, and the filtrate concentrated in vacuum. The resulting solid was swished with hexane/ethyl acetate (6:1) to give 14.5 g (84%) of the desired solid as a white solid.

Example 3

Preparation of 2-Bromo-2-(4-methylsulfonylphenyl)-1-(4-fluorophenyl)ethanone (Intermediate II, $R^1=CH_3$, $R^4=R^5=H$, $R^6=F$)

A mixture of 1-(4-fluorophenyl)-2-(4-methylsulfonyl phenyl)ethanone (14.6 g, 50 mmol) in 210 mL of chloroform and 826 mL of $CCl_4$. A solution of 8.0 g (50 mmol) of bromine in $CCl_4$ was added dropwise to the mixture. When the loss of the bromine colour was complete, the organic layer was washed with 5% aqueous sodium bicarbonate solution and with brine. It was dried over anhydrous sodium sulfate. The drying agent was filtered, and the filtrate concentrated in vacuum to give 14.0 g (70%) of the desired product as a solid.

Example 4

Preparation of 2-Bromo-2-(4-methylsulfonylphenyl)-1-(4-methoxyphenyl)ethanone (Intermediate II, $R^1=CH_3$, $R^4=R^5=H$, $R^6=MeO$)

The title compound was obtained from anisole and 4-methylthiophenylacetic chloride in chloroform, using the method of Examples 1, 2 and 3.

Example 5

Preparation of 2-Bromo-2-(4-methylsulfonylphenyl)-1-phenylethanone (Intermediate II, $R^1=CH_3$, $R^4=R^5=R^6=H$)

The title compound was obtained from benzene and 4-methylthiophenylacetic chloride, using the method of Examples 1, 2 and 3.

Example 6

Preparation of 2-Bromo-1-(3-fluoro-4-methoxyphenyl)-2-(4-methylsulfonylphenyl)ethanone (Intermediate II, $R^1=CH_3$, $R^4=H$, $R^5=F$, $R^6=MeO$)

The title compound was obtained from 2-fluoroanisole and 4-methylthiophenylacetic chloride in chloroform, using the method of Examples 1, 2 and 3.

Example 7

Preparation of 2-Bromo-1-(3-chloro-4-methoxyphenyl)-2-(4-methylsulfonylphenyl)ethanone (Intermediate II, $R^1=CH_3$, $R^4=H$, $R^5=Cl$, $R^6=MeO$)

The title compound was obtained from 2-chloroanisole and 4-methylthiophenylacetic chloride in chloroform, using the method of Examples 1, 2 and 3.

Example 8
Preparation of 3-(4-Methylsulfonylphenyl)-2-(4-fluorophenyl)imidazo[1,2a]pyrimidine (Product Ic)

A solution of 3.0 g of 2-bromo-2-(4-methylsulfonyl phenyl)-1-(4-fluorophenyl)ethanone (intermediate II, $R^1=CH_3$, $R^4=R^5=H$, $R^6=F$) in 300 mL of tert-butyl alcohol was treated with 15.0 g of 2-aminopyrimidine. The mixture reaction was refluxed for 16 h, and then it was allowed to cool. After concentration, the residue was treated with dichloromethane and 5% aqueous sodium bicarbonate solution. The organic layer was separated and washed with 5% aqueous sodium bicarbonate solution and water. The organic layer was dried over anhydrous sodium sulfate. The drying agent was filtered, and the filtrate concentrated in vacuum. The resulting residue was swished with acetone to give 1.1 g (37%) of the desired solid as a white solid.

Example 9
Preparation of 2-(4-Fluorophenyl)-3-(4-methylsulfonylphenyl)imidazo[1,2a][1,2,4]triazine (product Ibb)

A solution of 3.0 g de 2-bromo-2-(4-methylsulfonylphenyl)-1-(4-fluorophenyl)ethanone (intermediate II, $R^1=CH_3$, $R^4=R^5=H$, $R^6=F$) in 200 mL of acetonitrile was treated with 10.0 g of 3-amino [1,2,4] triazine. The reaction mixture was refluxed for 16 h. After cooling and removal of the solvent, the resulting residue was treated with dichloromethane and 5% aqueous sodium bicarbonate solution. The organic layer was separated and washed with 5% aqueous sodium bicarbonate solution and water. The organic layer was dried over anhydrous sodium sulfate. The drying agent was filtered, and the filtrate concentrated in vacuum. The resulting residue was swished with acetone to give 1.4 g (47%) of the desired solid as a yellow solid.

Example 10
Preparation of 2-(4-Fluorophenyl)-3-(4-methylsulfonylphenyl)imidazo[1,2a]pyridine (Product Ibbb)

A solution of 3.0 g of 2-bromo-2-(4-methylsulfonylphenyl)-1-(4-fluorophenyl)ethanone (intermediate II, $R^1=CH_3$, $R^4=R^5=H$, $R^6=F$) in 200 mL of acetonitrile was treated with 6.0 g of 2-aminopyridine. The mixture was refluxed for 12 h, and then it was allowed to cool. After concentration, the residue was treated with dichloromethane and 5% aqueous sodium bicarbonate solution. The organic layer was separated and washed with 5% aqueous sodium bicarbonate solution and water. The organic layer was dried over anhydrous sodium sulfate. The drying agent was filtered, and the filtrate concentrated in vacuum. The resulting residue was swished with isopropanol to give 0.94 g (32%) of the desired solid as a grey solid.

Example 11
Preparation of 2-(4-Methoxyphenyl)-3-(4-methylsulfonylphenyl)imidazo[1,2a]pyrimidine (Product If)

The title compound was obtained from 2-bromo-2-(4-methylsulfonylphenyl)-1-(4-methoxyphenyl)ethanone (intermediate II, $R^1=CH_3$, $R^4=R^5=H$, $R^6=MeO$) and 2-aminopyrimidine, using the method of Example 8.

Example 12
Preparation of 2-(4-Methoxyphenyl)-3-(4-methylsulfonylphenyl)imidazo[1,2a][1,2,4]triazine The title compound was obtained from 2-bromo-2-(4-methylsulfonylphenyl)-1-(4-methoxyphenyl)ethanone (intermediate II, $R^1=CH_3$, $R^4=R^5=H$, $R^6=MeO$) and 3-amino[1,2,4]triazine, using the method of Example 9.

Example 13
Preparation of 2-(4-Methoxyphenyl)-3-(4-methylsulfonylphenyl)imidazo[1,2a]pyridine (Product Iccc)

The title compound was obtained from 2-bromo-2-(4-methylsulfonylphenyl)-1-(4-methoxyphenyl)ethanone (intermediate II, $R^1=CH_3$, $R^4=R^5=H$, $R^6=MeO$) and 2-aminopyridine, using the method of Example 10.

Example 14
Preparation of 2-Phenyl-3-(4-methylsulfonylphenyl) imidazo[1,2a]pyrimidine (Product Ia)

The title compound was obtained from 2-bromo-2-(4-methylsulfonylphenyl)-1-phenylethanone (intermediate II, $R^1=CH_3$, $R^4=R^5=R^6=H$) and 2-aminopyrimidine, using the method of Example 8.

Example 15
Preparation of 2-Phenyl-3-(4-methylsulfonylphenyl) imidazo[1,2a][1,2,4]triazine (Product Iaa)

The title compound was obtained from 2-bromo-2-(4-methylsulfonylphenyl)-1-phenylethanone (intermediate II, $R^1=CH_3$, $R^4=R^5=R^6=H$) and 3-amino[1,2,4] triazine, using the method of Example 9.

Example 16
Preparation of 2-Phenyl-3-(4-methylsulfonylphenyl) imidazo[1,2a]pyridine (Product Iaaa)

The title compound was obtained from 2-bromo-2-(4-methylsulfonylphenyl)-1-phenylethanone (intermediate II, $R^1=CH_3$, $R^4=R^5=R^5=H$) and 2-aminopyridine, using the method of Example 10.

Example 17
Preparation of 2-(3-Fluoro-4-methoxyphenyl)-3-(4-methylsulfonylphenyl)-imidazo[1,2a]pyrimidine (Product Ij)

The title compound was obtained from 2-bromo-1-(3-fluoro-4-methoxyphenyl)-2-(4-methylsulfonylphenyl)-ethanone (intermediate II, $R^1=CH_3$, $R^4=H$, $R^5=F$, $R^6=MeO$) and 2-aminopyrimidine, using the method of Example 8.

Example 18
Preparation of 2-(3-Fluoro-4-methoxyphenyl)-3-(4-methylsulfonylphenyl)imidazo[1,2a][1,2,4]triazine (Product Icc)

The title compound was obtained from 2-bromo-1-(3-fluoro-4-methoxyphenyl)-2-(4-methylsulfonylphenyl) ethanone (intermediate II, $R^1=CH_3$, $R^4=H$, $R^5=F$, $R^6=MeO$) and 3-amino[1,2,4]triazine, using the method of Example 9.

Example 19
Preparation of 2-(3-Fluoro-4-methoxyphenyl)-3-(4-methylsulfonylphenyl)imidazo[1,2a]pyridine (Product Iggg)

The title compound was obtained from 2-bromo-1-(3-fluoro-4-methoxyphenyl)-2-(4-methylsulfonylphenyl) ethanone (intermediate II, $R^1=CH_3$, $R^4=H$, $R^5=F$, $R^6=MeO$) and 2-aminopyridine, using the method of Example 10.

Example 20
Preparation of 2-(3-Chloro-4-methoxyphenyl)-3-(4-methylsulfonylphenyl)imidazo[1,2a]pyridine (Product Ik)

The title compound was obtained from 2-bromo-1-(3-chloro-4-methoxyphenyl)-2-(4-methylsulfonylphenyl) ethanone (intermediate II, $R^1=CH_3$, $R^4=H$, $R^5=Cl$, $R^6=MeO$) and 2-aminopyrimidine, using the method of Example 8.

Example 21
Preparation of 2-(3-Chloro-4-methoxyphenyl)-3-(4-methylsulfonylphenyl)imidazo[1,2a][1,2,4]triazine (Product Iee)

The title compound was obtained from 2-bromo-1-(3-chloro-4-methoxyphenyl)-2-(4-methylsulfonyl phenyl) ethanone (intermediate II, $R^1=CH_3$, $R^4=H$, $R^5=Cl$, $R^6=MeO$) and 3-amino[1,2,4]triazine, using the method of Example 9.

Example 22
Preparation of 2-(3-Chloro-4-methoxyphenyl)-3-(4-methylsulfonylphenyl)imidazo[1,2a]pyridine (Product Ihhh)

The title compound was obtained from 2-bromo-1-(3-chloro-4-methoxyphenyl)-2-(4-methylsulfonylphenyl) ethanone (intermediate II, $R^1=CH_3$, $R^4=H$, $R^5=Cl$, $R_6=MeO$) and 2-aminopyridine, using the method of Example 10.

Example 23
Preparation of 2-(4-Aminosulfonylphenyl)-1-phenylethanone (Intermediate 7, $R^4=R^5=R^6=H$)

To 200 mL of chlorosulfonic acid, previously cooled to 0° C. with an icy brine solution, it was added portionwise 45.0 g of 1,2-diphenylethanone. The reaction mixture was stirred for 14 h at room temperature and poured into 900 g of ice, using vigorous mechanical stirring. The white precipitate appeared was filtered and added to a previously cooled mixture of acetone (67 mL) and ammonium solution in water (62 mL). The reaction mixture was stirred for 5 h at room temperature, filtered and washed with water. The resulting solid was swished with refluxing acetone for 30 min. It was filtered and vacuum dried in presence of phosphorous pentoxide, to give 22.5 g (36.0%) of the desired solid as a white powdered solid.

Example 24
Preparation of 2-(4-Aminosulfonylphenyl)-2-bromo-1-phenylethanone (Intermediate II, $R^1=NH_2$, $R^4=R^5=R^6=H$)

To a mixture of 14.4 g (52 mmol) of 2-(4-aminosulfonylphenyl)-1-phenylethanone in 240 mL of glacial acetic acid stirred under nitrogen, a solution of 24 mL of hydrobromic acid in glacial acetic acid (33%) was added. To the reaction mixture was added slowly 8.4 g (52 mmol) of bromine. It was stirred at room temperature until complete loss of the colour. After concentration, the resulting residue was dissolved in ethyl acetate (500 mL). The organic layer was washed twice with 5% aqueous sodium bicarbonate solution (2×350 mL) and with brine (350 mL). The organic layer was dried, filtered and concentrated in vacuum. The residue was swished in hexane to give 14.9 g (80%) of the desired solid as a white powdered solid.

Example 25
Preparation of 2-Phenyl-3-(4-aminosulfonylphenyl)imidazo[1,2a]pyridine (Product Irrr)

A mixture of 2.0 g of 2-(4-aminosulfonylphenyl)-2-bromo-1-phenylethanone in 120 mL of acetonitrile was treated with 6.0 g of 2-aminopyridine. It was refluxed until completion of the reaction, allowed to cool to room temperature and vacuum concentrated. The resulting residue was dissolved in ethyl acetate and washed with 5% aqueous sodium bicarbonate solution. The organic layer was dried, the drying agent filtered, and the filtrate vacuum evaporated. The resulting solid was swished with diethyl ether to give 640 mg (32%) of the desired compound as a pale brown powdered solid.

Example 26
Preparation of 2-Phenyl-3-(4-aminosulfonylphenyl)imidazo[1,2a]pyrimidine A mixture of 2.0 g of 2-bromo-2-(4-aminosulfonylphenyl)-1-phenylethanone in 120 mL of acetonitrile was treated with 6.0 g of 2-aminopyrimidine. The mixture was refluxed until completion of the reaction. The reaction mixture was allowed to cool to room temperature, and vacuum evaporated. The resulting residue was dissolved in ethyl acetate and washed with 5% aqueous sodium bicarbonate solution. The organic layer was dried, filtered and vacuum concentrated. The resulting solid was treated with diethyl ether and filtered to give 820 mg (42%) of the desired compound as a powdered yellow solid.

Example 27
Preparation of 2-Phenyl-3-(4-aminosulfonylphenyl)imidazo[1,2a][1,2,4]triazine (Product Idd)

A mixture of 4.0 g of 2-bromo-2-(4-aminosulfonylphenyl)-1-phenylethanone in 200 mL of acetonitrile was treated with 10.0 g of 3-amino[1,2,4]triazine. The mixture was refluxed until end of reaction, controlled by thin layer chromatography. After vacuum concentration, the resulting solid was treated with ethyl acetate and 5% aqueous sodium bicarbonate solution. The organic layer was separated and washed with 5% aqueous sodium bicarbonate solution, and once with brine. The organic layer was dried, the drying agent filtered, and the filtrate vacuum concentrated. The resulting residue was swished with diethyl ether and with hot ethanol, and filtered to give 1.9 g (48%) of the desired compound as a pale brown powdered solid.

Example 28
Preparation of 2-(4-Aminosulfonylphenyl)-1-(4-methoxyphenyl)ethanone (Intermediate 7, $R^4=R^5=H$, $R^6=OCH_3$)

The title compound was obtained from 2-phenyl-1-(4-methoxyphenyl)ethanone as a pale yellow powdered solid, using the method of Example 23.

Example 29
Preparation of 2-(4-Aminosulfonylphenyl)-2-bromo-1-(4-methoxyphenyl)ethanone (Intermediate II, $R^1=NH_2$, $R^4=R^5=H$, $R^6=OCH_3$)

The title compound was obtained from 2-(4-aminosulfonylphenyl)-1-(4-methoxyphenyl)ethanone as a yellow powdered solid, using the method of Example 24.

Example 30
Preparation of 2-(4-Methoxyphenyl)-3-(4-aminosulfonylphenyl)imidazo[1,2a]pyridine (Product Ittt)

The title compound was obtained from 2-(4-aminosulfonylphenyl)-2-bromo-1-(4-methoxyphenyl) ethanone as a pale yellow powdered solid, using the method of Example 25.

Example 31
Preparation of 2-(4-Methoxyphenyl)-3-(4-aminosulfonylphenyl)imidazo[1,2a]pyrimidine The title compound was obtained from 2-(4-aminosulfonylphenyl)-2-bromo-1-(4-methoxyphenyl) ethanone as a yellow powdered solid, using the method of Example 26.

Example 32
Preparation of 2-(4-Methoxyphenyl)-3-(4-aminosulfonylphenyl)imidazo[1,2a][1,2,4]triazine The title compound was obtained from 2-(4-aminosulfonylphenyl)-2-bromo-1-(4-methoxyphenyl)ethanone as a yellow powdered solid, using the method of Example 27.

Example 33
Preparation of 2-(4-Aminosulfonylphenyl)-1-(4-methylphenyl)ethanone (Intermediate 7, $R^4=R^5=H$, $R^6=CH_3$)

The title compound was obtained from 2-phenyl-1-(4-methylphenyl)ethanone as a pale yellow powdered solid, using the method of Example 23.

Example 34
Preparation of 2-(4-Aminosulfonylphenyl)-2-bromo-1-(4-methylphenyl)ethanone (Intermediate II, $R^1=NH_2$, $R^4=R^5=H$, $R^6=CH_3$)

The title compound was obtained from 2-(4-aminosulfonylphenyl)-1-(4-methylphenyl)ethanone as a white powdered solid, using the method of Example 24.

Example 35
Preparation of 2-(4-Methylphenyl)-3-(4-aminosulfonylphenyl)imidazo[1,2a]pyrimidine (Product Io)

The title compound was obtained from 2-(4-aminosulfonylphenyl)-2-bromo-1-(4-methylphenyl)ethanone as a pale brown powdered solid, using the method of Example 26.

Example 36
Preparation of 2-(4-Aminosulfonylphenyl)-1-(4-fluorophenyl)ethanone (Intermediate 7, $R^4=R^5=H$, $R^6=F$)

The title compound was obtained from 2-phenyl-1-(3-fluorophenyl)ethanone as a white powdered solid, using the method of Example 23.

Example 37
Preparation of 2-(4-Aminosulfonylphenyl)-2-bromo-1-(4-fluorophenyl)ethanone (Intermediate II, $R^1=NH_2$, $R^4=R^5=H$, $R^6=F$)

The title compound was obtained from 2-(4-aminosulfonylphenyl)-1-(4-fluorophenyl)ethanone as a pale brown hygroscopic powdered solid, using the method of Example 24.

Example 38
Preparation of 2-(4-Fluorophenyl)-3-(4-aminosulfonylphenyl)imidazo[1,2a]pyridine (Product Isss)

The title compound was obtained from 2-(4-aminosulfonylphenyl)-2-bromo-1-(4-fluorophenyl)ethanone as a pale yellow powdered solid, using the method of Example 25.

Example 39
Preparation of 2-(4-Fluorophenyl)-3-(4-aminosulfonylphenyl)imidazo[1,2a]pyrimidine The title compound was obtained from 2-(4-aminosulfonylphenyl)-2-bromo-1-(4-fluorophenyl)ethanone as a pale yellow powdered solid, using the method of Example 26.

Example 40
Preparation of 2-(4-Fluorophenyl)-3-(4-aminosulfonylphenyl)imidazo[1,2a][1,2,4]triazine The title compound was obtained from 2-(4-aminosulfonylphenyl)-2-bromo-1-(4-fluorophenyl)ethanone as a pale brown-green powdered solid, using the method of Example 27.

Example 41
Preparation of 2-(4-Aminosulfonylphenyl)-1-(3-chloro-4-methoxyphenyl)ethanone (Intermediate 7, $R^4=H$, $R^5=Cl$, $R^6=OCH_3$)

The title compound was obtained from 2-phenyl-1-(3-chloro-4-methoxyphenyl)ethanone as a pale yellow powdered solid, using the method of Example 23.

Example 42
Preparation of 2-(4-Aminosulfonylphenyl)-2-bromo-1-(3-chloro-4-methoxyphenyl)ethanone (Intermediate II, $R^1=NH_2$, $R^4=H$, $R^5=Cl$, $R^6=OCH_3$)

The title compound was obtained from 2-(4-aminosulfonylphenyl)-1-(3-chloro-4-methoxyphenyl)ethanone as a pale brown powdered solid, using the method of Example 24.

Example 43
Preparation of 2-(3-Chloro-4-methoxyphenyl)-3-(4-aminosulfonylphenyl)imidazo[1,2a]pyridine (Product Iwww)

The title compound was obtained from 2-(4-aminosulfonylphenyl)-2-bromo-1-(3-chloro-4-methoxyphenyl)ethanone as a pale yellow powdered solid, using the method of Example 25.

Example 44
Preparation of 2-(4-Aminosulfonylphenyl)-1-(3-fluoro-4-methoxyphenyl)ethanone (Intermediate 7, $R^4=H$, $R^5=F$, $R^6=OCH_3$)

The title compound was obtained from 2-phenyl-1-(3-fluoro-4-methoxyphenyl)ethanone as a pale brown powdered solid, using the method of Example 23.

Example 45
Preparation of 2-(4-Aminosulfonylphenyl)-2-bromo-1-(3-fluoro-4-methoxyphenyl)ethanone (Intermediate II, $R^1=NH_2$, $R^4=H$, $R^5=F$, $R^6=OCH_3$)

The title compound was obtained from 2-(4-aminosulfonylphenyl)-1-(3-fluoro-4-methoxyphenyl)ethanone as a pale brown powdered solid, using the method of Example 24.

Example 46
Preparation of 2-(3-Fluoro-4-methoxyphenyl)-3-(4-aminosulfonylphenyl)imidazo[1,2a]pyrimidine (Product Ip)

The title compound was obtained from 2-(4-aminosulfonylphenyl)-2-bromo-1-(3-fluoro-4-methoxyphenyl)ethanone as a pale yellow powdered solid, using the method of Example 26.

Example 47
Preparation of 2-Phenyl-1-(3-fluorophenyl)ethanol (Intermediate 9, $R^4=R^6=H$, $R^5=F$)

Magnesium powder (12.8 g, 527 mmol) was covered with 30 mL of the solution previously prepared of 82.6 g (483 mmol) of benzyl bromide in 500 mL of diethyl ether. Once the reaction was started, the rest of the solution was added in such a rate that the reflux did not stop during the addition. When the addition was finished, the reaction mixture was stirred at reflux for 30 minutes, and cooled to 0° C. A mixture of 50.0 g (403 mmol) of 3-fluorobenzaldehyde in 250 mL of diethyl ether was added to the reaction mixture. It was stirred at room temperature until completion of the reaction. The mixture was treated then with 300 mL of a saturated aqueous ammonium chloride solution. The organic layer was separated and washed successively with 500 mL of a 40% aqueous sodium bisulfide solution (twice), 500 mL of a 5% aqueous sodium bicarbonate solution, and 300 mL of water. The organic layer was dried, the drying agent filtered, and the filtrate vacuum evaporated to give 80.4 g (93%) of the title compound as a yellow oil suitable for use without further purification.

Example 48
Preparation of 2-Phenyl-1-(3-fluorophenyl)ethanone (Intermediate 6, $R^4=R^6=H$, $R^5=F$)

Pyridinium chlorochromate 113.4 g (526 mmol) was added to a cool (0° C.) solution of 75.7 g (350 mmol) of 2-phenyl-1-(3-fluorophenyl)ethanol in 1.5 L of dichloromethane. The mixture was stirred for 3 h at room temperature, and the reaction mixture was then purified by filtration through silica gel (silica/reaction mixture, 10:1) using a mixture of ethyl acetate and hexane (1:10) as the eluent to give 26.1 g (35%) of the title compound as a white solid.

Example 49
Preparation of 2-(4-Aminosulfonylphenyl)-1-(3-fluorophenyl)ethanone (Intermediate 7, $R^4=R^6=H$, $R^5=F$)

To 85.1 mL of chlorosulfonic acid, previously cooled to −5° C., it was added portionwise 20.4 g of 2-phenyl-1-(3-fluoro phenyl)ethanone. The reaction mixture was stirred for 20 h at room temperature and poured into 2.2 kg of ice. This mixture was stirred for 2 h and extracted twice with ethyl acetate (2×850 mL). The organic layer was washed three times with 950 mL of brine and treated with 215 mL of ammonia. The resulting mixture was stirred for 1 h. The organic layer was separated and washed for four times with 300 mL of 2N aqueous hydrochloric acid solution, and twice with 300 mL of brine. The organic layer was dried, the drying agent filtered and the filtrate vacuum evaporated. The resulting residue was swished with diethyl ether to give 8.3 g (30%) of the title compound.

Example 50
Preparation of 2-Bromo-2-(4-aminosulfonylphenyl)-1-(3-fluorophenyl)ethanone (Intermediate II, $R^1=NH_2$, $R^4=R^6=H$, $R^5=F$)

A mixture of 39 mL of hydrobromic acid 33% in glacial acetic acid was added to a solution of 8.2 g (22 mmol) of 2-(4-aminosulfonylphenyl)-1-(3-fluorophenyl)ethanone in 157 mL of glacial acetic acid under a nitrogen atmosphere. After the end of the addition 3.5 g (22 mmol) of bromine were added dropwise to the mixture. The reaction mixture was stirred for 3 h at room temperature and poured into 600 mL of water. The mixture was stirred for 45 minutes, filtered and gently washed with water. The resulting solid was dissolved in ethyl acetate and washed five times with 100 mL of 5% aqueous sodium bicarbonate solution and three times with 150 mL of brine. The organic layer was dried over sodium sulfate, filtered, and the filtrate vacuum concentrated. The resulting residue was swished with 50 mL of hexane to give 5.7 g (54%) of the title compound.

Example 51
Preparation of 2-(3-Fluorophenyl)-3-(4-aminosulfonylphenyl)imidazo[1,2a][1,2,4]triazine (Product Ihh)

A mixture of 2.0 g of 2-bromo-2-(4-aminosulfonylphenyl)-1-(3-fluorophenyl)ethanone, 8.0 g of 3-amino-1,2,4-triazine and 300 mL of ethanol were refluxed under nitrogen atmosphere until completion of reaction. The reaction mixture was cooled and purified by filtration through silica. It was concentrated and the resulting solid was dissolved in 200 mL of dichlorometane. The organic layer was washed with 150 mL of 5% aqueous sodium bicarbonate solution and with 150 mL of water. The resulting residue was swished first with hexane and with isopropanol later, to give 270 mg (13%) of the title compound.

Example 52
Preparation of 2-(3-Fluorophenyl)-3-(4-aminosulfonylphenyl)imidazo[1,2a]pyrimidine (Product It)

A mixture of 2.0 g of 2-bromo-2-(4-aminosulfonylphenyl)-1-(3-fluorophenyl)ethanone, 8.0 g of 2-aminopyrimidine and 300 mL of ethanol were refluxed under a nitrogen atmosphere until completion of the reaction. The reaction mixture was cooled and purified by filtration through silica. It was concentrated and the resulting solid was dissolved in 200 mL of ethyl acetate. The organic layer was washed with 150 mL of 5% aqueous sodium bicarbonate solution and with 150 mL of water. The resulting residue was swished first with hexane and with isopropanol later, to give 1.1 g (55%) of the title compound.

Example 53
Preparation of 2-(3-Fluorophenyl)-3-(4-aminosulfonylphenyl)imidazo[1,2a]pyridine (Product Iqqq)

A mixture of 1.4 g of 2-bromo-2-(4-aminosulfonylphenyl)-1-(3-fluorophenyl)ethanone, 7.5 g of 2-aminopyridine and 300 mL of ethanol were refluxed under a nitrogen atmosphere until completion of the reaction. The reaction mixture was cooled and purified by filtration through silica. It was concentrated and the resulting solid was dissolved in 200 mL of ethyl acetate. The organic layer was washed with 150 mL of 5% aqueous sodium bicarbonate solution and with 150 mL of water. The resulting residue was swished first with hexane and with isopropanol later, to give 940 mg (55%) of the title compound.

Example 54
Assay for in vitro COX-2 Inhibition

Human whole blood from volunteers with no apparent inflammatory conditions and not having taken any NSAIDs for at least 15 days prior to blood collection was used to evaluate the COX-2 inhibitory effect of the synthesized compounds. Blood aliquots of 500 µL were incubated with either DMSO (vehicle) or the test compounds at final concentrations varying from 0.1 to 25 µM, for 15 minutes at 37° C. Subsequetly, 5 µL of LPS (Lipopolysacharide from E.Choli, serotipe: 0111:B4, SIGMA) were added at final concentrations of 100 µg/mL for 24 h at 37° C. to induce COX-2. At the end of the incubation, the blood was centrifuged at 10.000 rpm to obtain plasma, and the samples were stored at −80° C. $PGE_2$ levels in plasma were established using EIA (Cayman Chemical). Results are shown as $CI_{50}$ in Table 1.

Example 55
Assay for in vitro COX-1 Inhibition

Fresh blood was collected into sterile containers with no anticoagulants. Aliquots of 500 µL were immediately transferred to eppendorf tubes, preloaded with a test compound each, at final concentrations varying from 0.1 to 100 µM. The eppendorf tubes were vortexed and incubated at 37° C. for 1 hour. At the end of incubation, plasma was obtained by centrifugation and stored at −80° C. $TXB_2$ levels in plasma were established using EIA (Cayman Chemical). Results are shown as $CI_{50}$ in Table 1.

What is claimed is:
1. A imidazo[1,2-a]azine of formula (I), or a pharmaceutically acceptable solvate and acid addition salt thereof, wherein $R^1$ is selected from the group consisting of $CH_3$ and

NH$_2$; R$^2$ and R$^3$ are selected from the group consisting of H, CH$_3$, Cl, Br, COCH$_3$ and OCH$_3$; and R$^4$, R$^5$ and R$^6$ are each independently selected from the group consisting of H, F, Cl, Br, (C$_1$–C$_3$)-alkyl, trifluoromethyl, (C$_1$–C$_3$)-alkoxy and trifluoromethoxy

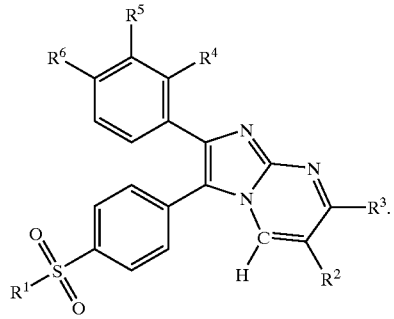

(I)

2. A compound according to claim 1, wherein R$^4$, R$^5$, and R$^6$ are selected from the group consisting of H, F, Cl, methyl, isopropyl, methoxy and ethoxy.

3. A compound according to claim 2, said compound being selected from the group consisting of:

(Ia) 2-phenyl-3-(4-methylsulfonylphenyl)imidazo[1,2-a]pyrimidine;
(Ib) 2-(4-methylphenyl)-3-(4-methylsulfonylphenyl)imidazo[1,2-a]pyrimidine;
(Ic) 2-(4-fluorophenyl)-3-(4-methylsulfonylphenyl)imidazo[1,2-a]pyrimidine;
(Id) 2-(4-chlorophenyl)-3-(4-methylsulfonylphenyl)imidazo[1,2-a]pyrimidine;
(Ie) 2-(4-bromophenyl)-3-(4-methylsulfonylphenyl)imidazo[1,2-a]pyrimidine;
(If) 2-(4-methoxyphenyl)-3-(4-methylsulfonylphenyl)imidazo[1,2-a]pyrimidine;
(Ig) 2-(4-ethoxyphenyl)-3-(4-methylsulfonylphenyl)imidazo[1,2-a]pyrimidine;
(Ih) 2-(3,4-dimethylphenyl)-3-(4-methylsulfonylphenyl)imidazo[1,2-a]pyrimidine;
(Ii) 2-(3-methyl-4-methoxyphenyl)-3-(4-methylsulfonylphenyl)imidazo[1,2-a]pyrimidine;
(Ij) 2-(3-fluoro-4-methoxyphenyl)-3-(4-methylsulfonylphenyl)imidazo[1,2-a]pyrimidine;
(Ik) 2-(3-chloro-4-methoxyphenyl)-3-(4-methylsulfonylphenyl)imidazo[1,2-a]pyrimidine;
(Il) 2-(3,4-dimethoxyphenyl)-3-(4-methylsulfonylphenyl)imidazo[1,2-a]pyrimidine;
(Im) 7-methyl-2-(4-methylphenyl)-3-(4-methylsulfonylphenyl)imidazo[1,2-a]pyrimidine;
(In) 7-methyl-2-(3,4-dimethylphenyl)-3-(4-methylsulfonylphenyl)imidazo[1,2-a]pyrimidine;
(Io) 2-(4-methylphenyl)-3-(4-aminosulfonylphenyl)imidazo[1,2-a]pyrimidine;
(Ip) 2-(3-fluoro-4-methoxyphenyl)-3-(4-aminosulfonylphenyl)imidazo[1,2-a]pyrimidine;
(Iq) 2-(2-methylphenyl)-3-(4-aminosulfonylphenyl)imidazo[1,2-a]pyrimidine;
(Ir) 2-(4-fluorophenyl)-3-(4-aminosulfonylphenyl)imidazo[1,2-a]pyrimidine;
(Is) 2-(2-chlorophenyl)-3-(4-aminosulfonylphenyl)imidazo[1,2-a]pyrimidine;
(It) 2-(3-fluorophenyl)-3-(4-aminosulfonylphenyl)imidazo[1,2-a]pyrimidine; and
(Iu) 2-(3-chlorophenyl)-3-(4-aminosulfonylphenyl)imidazo[1,2-a]pyrimidine.

4. A compound according to claim 3, said compound being 3-(4-methylsulfonylphenyl)-2-(4-fluorophenyl)imidazo[1,2-a]pyrimidine (Ic).

5. A compound according to claim 3, said compound being 3-(4-methylsulfonylphenyl)-2-(4-fluorophenyl)imidazo[1,2-a]pyrimidine (If).

6. A compound according to claim 3, said compound being 3-(4-methylsulfonylphenyl)-2-(4-ethoxyphenyl)imidazo[1,2-a]pyrimidine (Ig).

7. A pharmaceutical composition comprising a therapeutically effective amount of a compound of formula (I) as defined in claim 1, and suitable amounts of pharmaceutically acceptable carriers.

8. A pharmaceutical composition for treating rheumatoid arthritis, comprising a therapeutically effective amount of a compound of formula (I) as defined in claim 1, and suitable amounts of pharmaceutically acceptable carriers.

9. A pharmaceutical composition for treating a cancer, comprising a therapeutically effective amount of a compound of formula (I) as defined in claim 1, and suitable amounts of pharmaceutically acceptable carriers.

10. A method of treating rheumatoid arthritis in a subject comprising administering a therapeutic amount of a compound of formula (I), as defined in claim 1.

11. A method of treating cancer in a subject comprising administering a therapeutic amount of a compound of formula (I), as defined in claim 1.

12. A method according to claim 11, wherein the cancer is colon cancer.

13. A process for preparing a imidazo[1,2-a]azine of formula (I), as defined in claim 1, comprising the condensation reaction of a substituted 2-bromo-2-(4-R$^1$-sulfonylphenyl)-1-phenylethanone of formula (II) with a substituted aminoazine of formula (III), in a polar solvent.

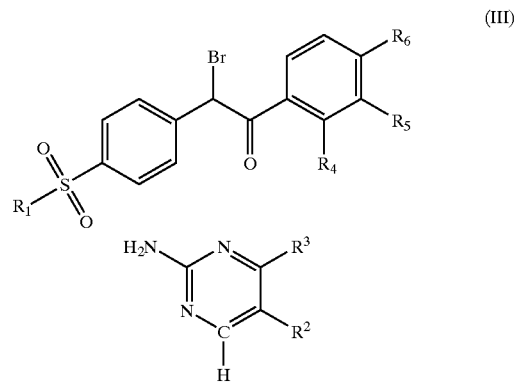

(III)

* * * * *